(12) United States Patent
Ahn

(10) Patent No.: US 10,201,468 B2
(45) Date of Patent: Feb. 12, 2019

(54) DEVICE FOR TREATING DRY EYE SYNDROME AND STRENGTHENING EYESIGHT

(71) Applicant: Seon Jong Ahn, Gyeonggi-do (KR)

(72) Inventor: Seon Jong Ahn, Gyeonggi-do (KR)

(*) Notice: Subject to any disclaimer, the term of this patent is extended or adjusted under 35 U.S.C. 154(b) by 206 days.

(21) Appl. No.: 15/512,735

(22) PCT Filed: Apr. 7, 2015

(86) PCT No.: PCT/KR2015/003452
§ 371 (c)(1),
(2) Date: Mar. 20, 2017

(87) PCT Pub. No.: WO2016/068412
PCT Pub. Date: May 6, 2016

(65) Prior Publication Data
US 2017/0296420 A1    Oct. 19, 2017

(30) Foreign Application Priority Data
Oct. 31, 2014  (KR) .................. 10-2014-0150010

(51) Int. Cl.
*A61F 9/00* (2006.01)
*A61H 5/00* (2006.01)
(Continued)

(52) U.S. Cl.
CPC .............. *A61H 5/00* (2013.01); *A61F 9/00* (2013.01); *A61F 9/029* (2013.01); *A61H 35/02* (2013.01); *A61H 2201/0119* (2013.01)

(58) Field of Classification Search
CPC .. A61H 5/00; A61H 35/02; A61H 2201/0119; A61H 5/005; A61F 9/029; A61F 9/00; A61B 3/00; A61B 3/032
(Continued)

(56) References Cited

U.S. PATENT DOCUMENTS 6,270,467 B1    8/2001  Yee
8,721,572 B1    5/2014  Linder et al.
(Continued)

FOREIGN PATENT DOCUMENTS

KR    20-0159302         10/1999
KR    200159302 Y1 *    10/1999
(Continued)

OTHER PUBLICATIONS

International Search Report dated Jun. 29, 2015 for PCT/KR2015/003452.

*Primary Examiner* — William R Alexander
*Assistant Examiner* — Henry A Duong

(57) ABSTRACT

A device for treating dry eye syndrome and strengthening eyesight, of the present invention, comprises: a water goggles main body part into which a saline solution is injected, and which is closely adhered to the facial surface of a user, thereby allowing muscular exercise of the eyeballs to be carried out in the saline solution; a saline solution container coupled to the upper part of the water goggles main body part so as to supply a predetermined amount of saline solution; and a display device fixed to the front of the saline solution container, and in which an ocular muscle strengthening program for guiding the user's line of vision is executed so as to enable eyeball exercise to be performed in the saline solution.

19 Claims, 8 Drawing Sheets

(51) Int. Cl.
*A61H 35/02* (2006.01)
*A61F 9/02* (2006.01)

(58) Field of Classification Search
USPC .......................................................... 351/203
See application file for complete search history.

(56) References Cited

U.S. PATENT DOCUMENTS

| 2008/0191965 A1* | 8/2008 | Pandozy | ................. | A61H 5/00 |
| | | | | 345/8 |
| 2013/0057536 A1* | 3/2013 | Li | ........................ | G06T 13/20 |
| | | | | 345/419 |

FOREIGN PATENT DOCUMENTS

| KR | 10-2002-0010344 | 2/2002 |
| KR | 10-2004-0090147 | 9/2004 |
| KR | 20-2009-0004023 | 4/2009 |

* cited by examiner

Enlarged drawing of "A" part

Enlarged drawing of "B" part

DEVICE FOR TREATING DRY EYE SYNDROME AND STRENGTHENING EYESIGHT

This application claims the priority of Korean Patent Application No. 10-2014-0150010, filed on Oct. 31, 2014 in the KIPO (Korean Intellectual Property Office), the disclosure of which is incorporated herein entirely by reference. Further, this application is the National Stage application of International Application No. PCT/KR2015/003452, filed Apr. 7, 2015, which designates the United States and was published in Korean. Each of these applications is hereby incorporated by reference in their entirety into the present application.

TECHNICAL FIELD

The present disclosure relates to a device for treating dry eye syndrome and strengthening eyesight. More particularly, the present disclosure relates to a device for treating dry eye syndrome and strengthening eyesight, in which a saline solution container for storing saline solution therein, and a water goggles main body part for administering saline solution only to eyeballs and facial area near the eyeballs, are configured so as to be separable, thus facilitating hygienic management of the therapeutic device, in which ocular muscle exercise is performed in the saline solution while in close adhesion against the water goggles main body part such that dry eye syndrome treatment can be performed freely in a comfortable condition, and in which, during ocular muscle exercise, eye cleanse is enabled to strengthen eyesight and also to remove waste from inside the eye, and in which dry eye syndrome can be prevented and treated at economic cost.

BACKGROUND ART

Recently, the number of patients with dry eye syndrome who complain eye dryness has rapidly increased. The dry eye syndrome is suffered after eyes are tired from intense use due to, for example, long-hour viewing of computer monitor, TV watching, and so on, or under considerably low humidity due to excessive indoor heating, or when eyes get dried as a symptom of presbyopia, and so on.

It was reported that, as a result of conducting eye cleansing two times a day, each for 30 seconds, for 10 days, specifically those with dry eye syndrome showed improvement of tear film breakup time (BUT) from 0 to 2 seconds to above 2 to 4 seconds (normal: 10 seconds), and it is also known that people maintained younger eyes than ordinary counterparts after regularly performed eye cleansing and eye exercise for 10 years.

The eye cleansing and exercise involves burying a face under distilled water and moving pupils up and down, left and right, and clockwise in order, while keeping eyes wide open. This procedure often causes pains because an exerciser has to hold his or her breath. Further, additional disadvantage is that the exerciser has to maintain inconvenient posture, and also keep a container in hygienic state, which is difficult. It is also necessary that a large amount of water is consumed.

Recently, a way of directly administering artificial tear to eyeball has been mainly used in order to alleviate inconveniences from dry eye syndrome. However, because artificial tear for frequent administration to eyeball is prescribed by a doctor and purchased at a pharmacy, a considerable amount of time and cost is necessary for purchasing artificial tears, not to mention inconveniences experienced in the process.

Accordingly, KR Utility Model No. 20-2009-0004023 has been proposed, disclosing humidifying glasses, which include a moisture inlet port with removable lid, being formed on a connection formed at a center of the glasses frame, and a moisture feeding pipe within lower frame on both sides of the glasses frame, being connected to the moisture inlet port, and a plurality of passing holes formed on an inner surface of the lower frame, through which water stored in the moisture feeding pipe is oozing outside, and a moisture absorption member for absorbing moisture oozing out of the passing holes in the inner surface of the both lower frames.

However, while the humidifying glasses described above can prevent eye dryness only for temporarily, the glasses will not be sufficient for the treatment purpose. Further, when the eyeballs and the passing holes are misaligned, efficiency may be dropped as the moisture is administered onto the face of the exerciser.

DISCLOSURE OF THE INVENTION

Technical Problem

According to an embodiment, a technical objective is to provide a device for treating dry eye syndrome and strengthening eyesight, which includes a saline solution container for storing saline solution therein, and a water goggles main body part for administering saline solution only to eyeballs and facial area near the eyeballs, in which the saline solution container and the water goggles main body part are configured so as to be separable, thus facilitating hygienic management of the therapeutic device, and in which ocular muscle exercise can be performed in the saline solution in close adhesion against the water goggles main body part such that dry eye syndrome treatment can be performed freely in a comfortable condition.

Further, a technical objective is to provide a device for treating dry eye syndrome and strengthening eyesight, in which, during ocular muscle exercise, eye cleanse is enabled to strengthen eyesight and also to remove waste from inside the eye, and dry eye syndrome can be prevented and treated at economic cost.

Further, a technical objective is to provide a device for treating dry eye syndrome and strengthening eyesight, capable of preventing and treating dry eye syndrome that may occur as the eyeballs age, and strengthening ocular muscles by way of ocular muscle (ciliary body) exercise, while also delaying or preventing weakening eyesight by stimulating blood circulation around eyes.

Technical Solution

In order to achieve the objects mentioned above, a device for treating dry eye syndrome and strengthening eyesight is provided, which may include a water goggles main body part into which a saline solution is injected and which is closely adhered to a facial surface of a user, thereby allowing muscular exercise of eyeballs to be carried out in the saline solution, a saline solution container coupled to an upper part of the water goggles main body part so as to supply a predetermined amount of saline solution, and a display device fixed to a front of the saline solution container, and in which an ocular muscle strengthening program for guiding the user's line of vision is executed so as to enable eyeball exercise to be performed in the saline solution.

Further, the water goggles main body part may include a mask part to which the saline solution is supplied from the saline solution container in a state in which the facial surface of the user is in position, a penetrating window formed of a transparent material, fixed to a front of the mask part, an adhesion pad for bringing the facial surface of a user to a close contact with the mask part, a securing band configured to allow the user to wear the water goggles main part on the user's head, and a saline solution feeding pipe protruding upward from an upper part of the mask part to be coupled with the saline solution container, to inject the saline solution into the mask part.

Further, the device may include a storage tank for storing the saline solution, a fixing part formed on the front of the storage tank to securely receive the display device inserted therein, a sealing lid openably formed on an upper part of the storage tank, a supply housing for supplying the stored saline solution into the water goggles main body part, and a feed rate adjusting part rotatably coupled with the supply housing to adjust a feed rate of the saline solution being supplied toward the water goggles main body part.

Further, the supply housing may include a rotation support inwardly protruded to be rotatably coupled with the feed rate adjusting part, an inlet hole through which the saline solution stored in the storage tank is introduced into the feed rate adjusting part, and a fixing groove coupled with the water goggles main body part to supply the saline solution stored in the storage tank toward the water goggles main body part.

Further, the feed rate adjusting part may include: an adjusting housing coupled at one end with the rotation support, and supplying the saline solution through a supply hole fluidly communicating with the inlet hole, in which the adjusting housing may include an opening and closing hole for discharging the supplied saline solution toward the water goggles main body part; and an adjusting switch formed at other end of the adjusting housing, to adjust a feed rate of the saline solution by controlling opening and closing of the opening and closing hole.

Further, the display device may include an ocular muscle strengthening part positioned in front of the water goggles main body part to perform an ocular muscle strengthening program, a line-of-vision guidance driving part for executing the ocular muscle strengthening program in association with the ocular muscle strengthening part to thus enable the user to perform an ocular muscle strengthening exercise, and an operation controller fixed to the saline solution container to control driving of the ocular muscle strengthening part and set duration of driving the line-of-vision guidance driving part and driving step thereof.

Further, the ocular muscle strengthening part and the operation controller may be rotatably coupled by a rotating axis.

Further, the device may additionally include a guidance indicating device in the ocular muscle strengthening part, in which the guidance indicating device may include a liquid crystal display (LCD) illuminated upon driving of the line-of-vision guidance driving part, and a LCD panel having the LCD installed therein.

Further, upon driving of the line-of-vision guidance driving part, the guidance indicating device may cause the LCD to be illuminated in an arrow-like form and repeated in directions in an order of up, down, left, right, clockwise, and rotating in a Figure-8 pattern.

Further, the operation controller may additionally include a fixing means formed on a rear face to fix the display device to the saline solution container.

Further, the operation controller may include a setting indicating part for outputting setting status of the line-of-vision guidance driving part, a driving setting part for setting an ocular muscle strengthening step of the ocular muscle strengthening program executed by the line-of-vision guidance driving part, and a timer setting part for setting a duration of driving the line-of-vision driving part.

Further, the driving setting part may include a power supply on/off button with which a user selects between driving and stopping, and when the line-of-vision guidance driving part is driven, the driving setting part may output an alarm for 0.2 second as a preparatory operation, notifying that the exercise will begin.

Advantageous Effects

The present disclosure provides an effect of ease of maintaining hygienic state since the saline solution container and the water goggles main body part are configured so as to be separable. Further, the present disclosure provides an effect that a user is able to treat dry eye syndrome while freely breathing in comfortable condition, while performing muscle exercise of the eyes in the saline solution in tight adhesion to the water goggles main body part.

Further, the present disclosure provides an effect in which, during ocular muscle exercise, an eye cleanse is enabled to strengthen eyesight and also to remove waste from inside the eye, and dry eye syndrome can be prevented and treated at economic cost.

Further, the present disclosure provides an effect of preventing and treating dry eye syndrome that may occur as the eyeballs age, and strengthening ocular muscles by way of ocular muscle exercise, while also delaying or preventing weakening eyesight by stimulating blood circulation around eyes.

MODE FOR CARRYING OUT THE INVENTION

Figure 1:
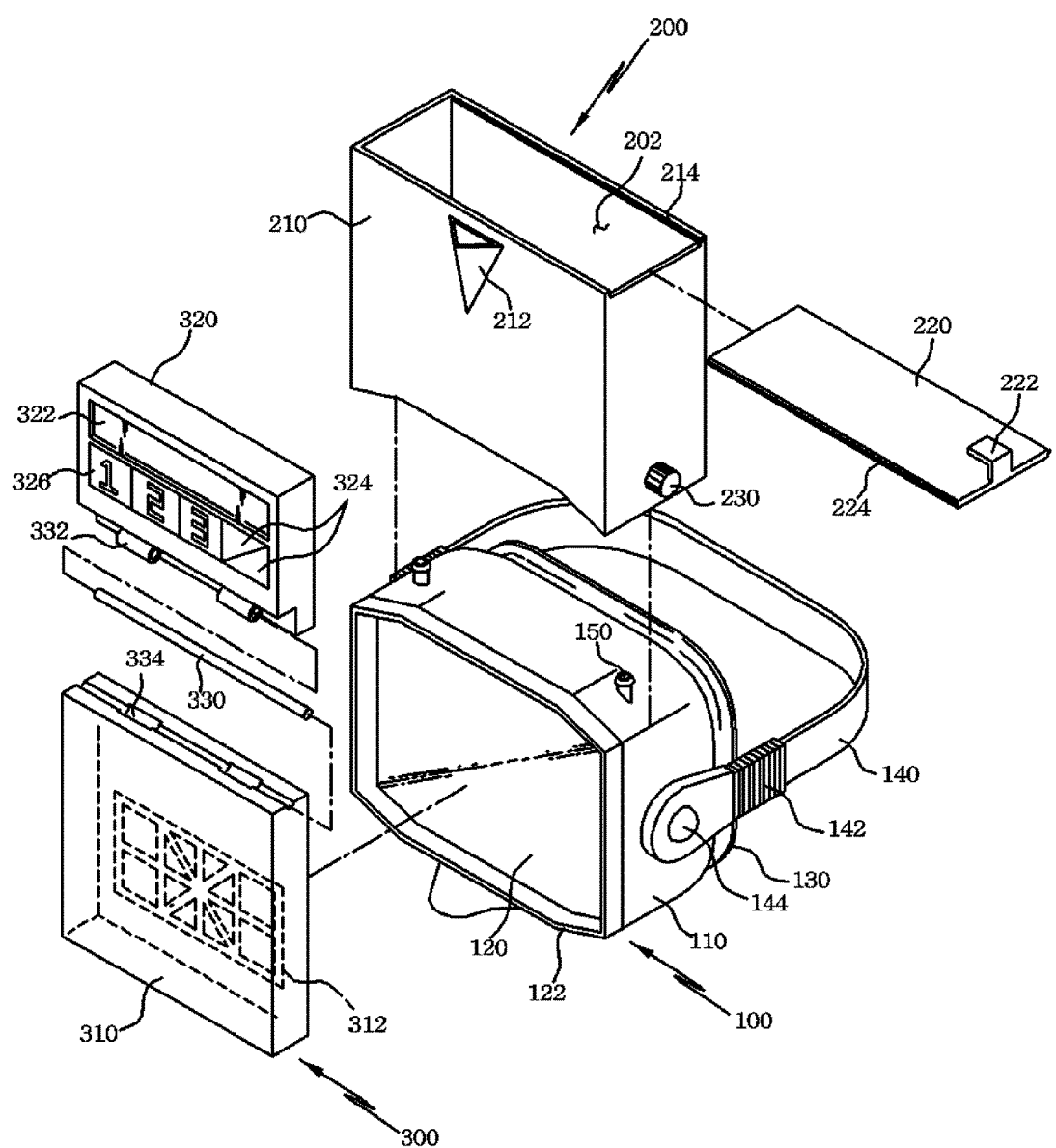
FIGS. 1 and 2 are perspective views of a device for treating dry eye syndrome and strengthening eyesight according to an exemplary embodiment of the present disclosure.

In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail.

Figure 2:
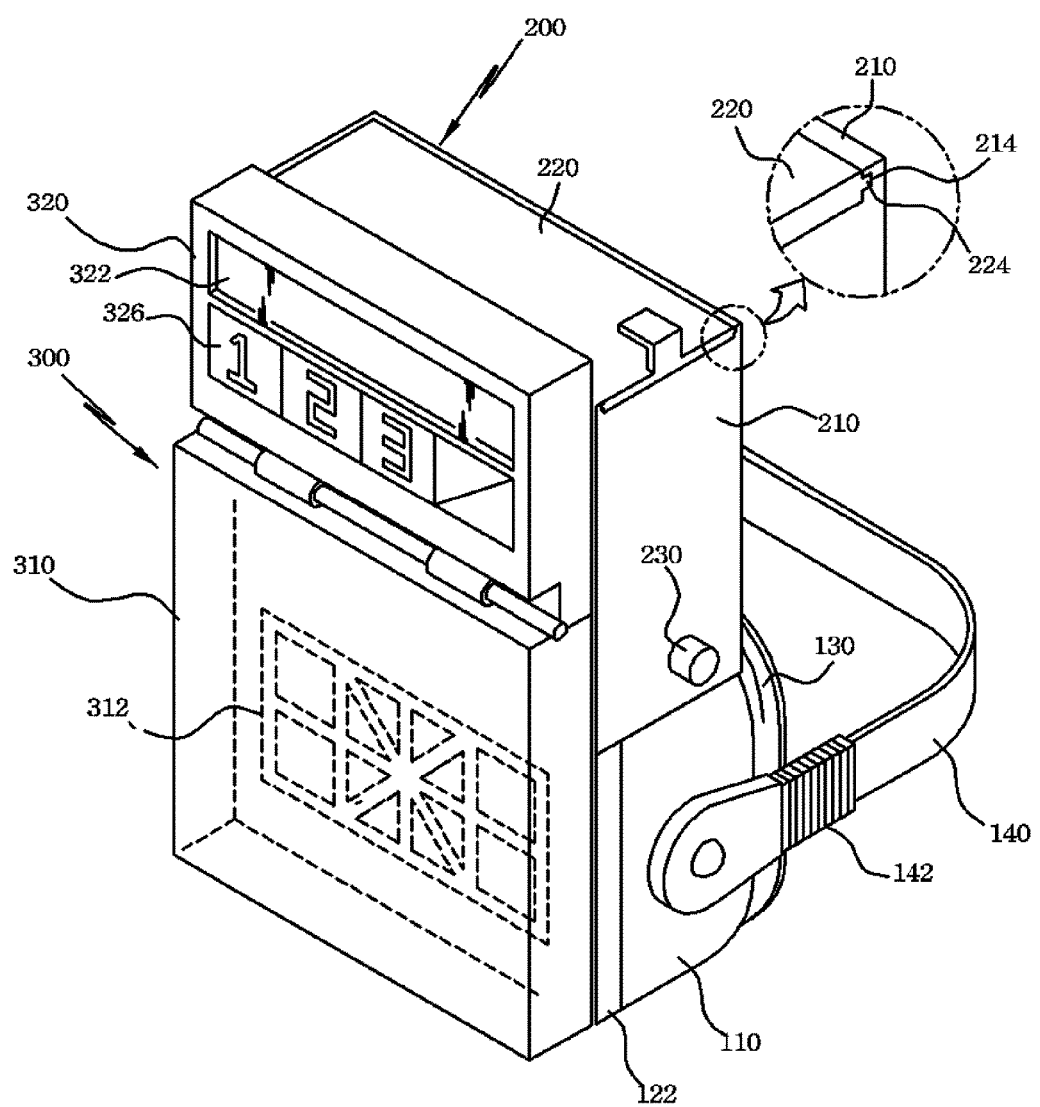
Figure 3:
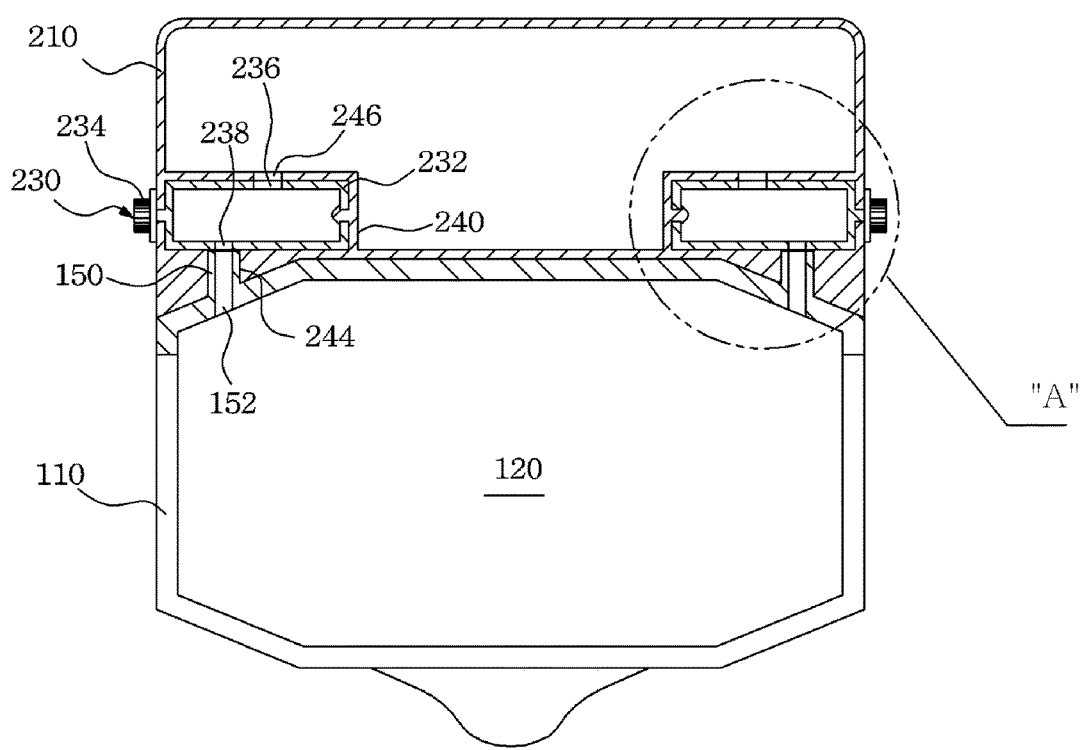
FIG. 3 is a cross-sectional view illustrating a device for treating dry eye syndrome and strengthening eyesight in an assembled state, according to an exemplary embodiment of the present disclosure.
Figure 4:
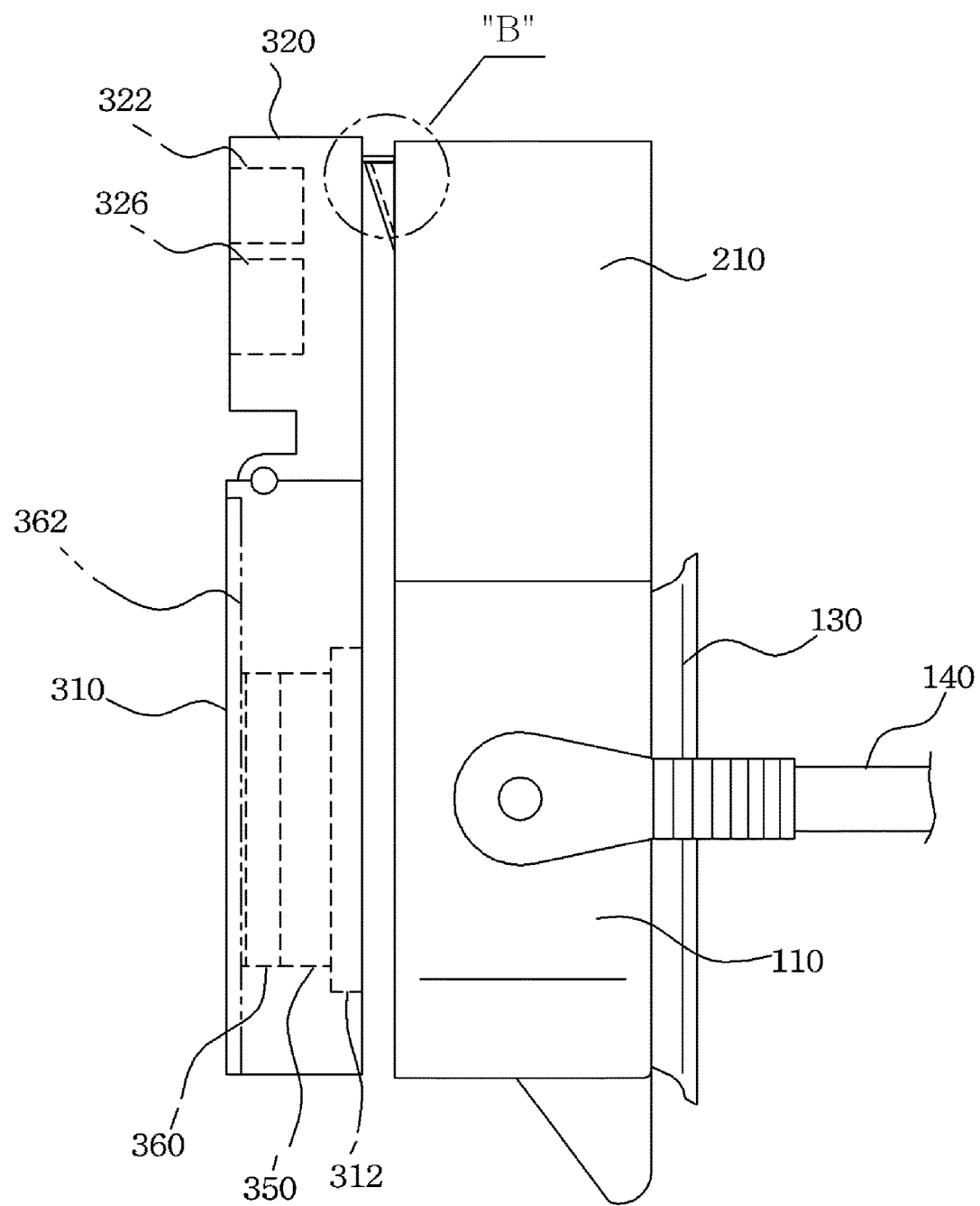
FIG. 4 is a side view of a device for treating dry eye syndrome and strengthening eyesight according to an exemplary embodiment of the present disclosure.
Figure 5A:
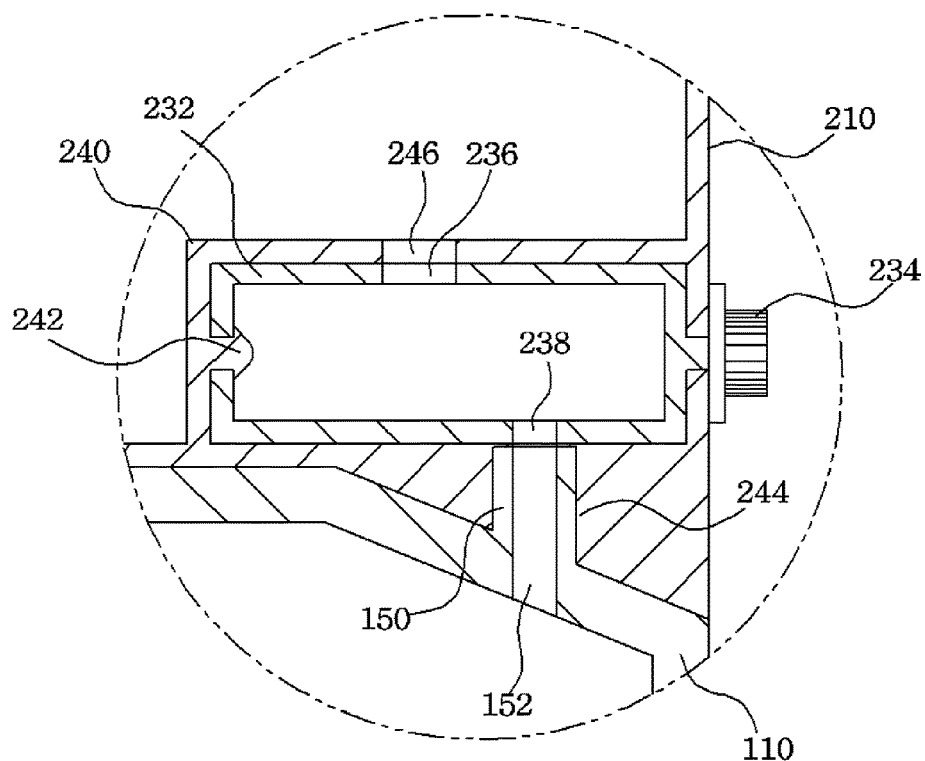
FIGS. 5A and 5B illustrate main portions of a device for treating dry eye syndrome and strengthening eyesight according to an exemplary embodiment of the present disclosure.
Figure 5B:
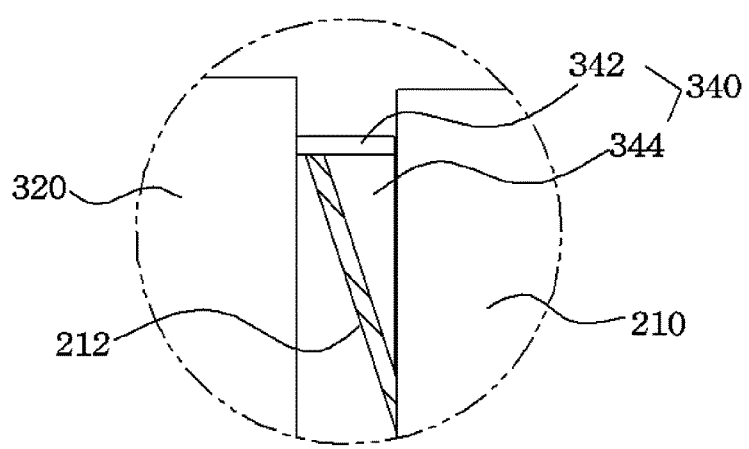
Figure 6A:
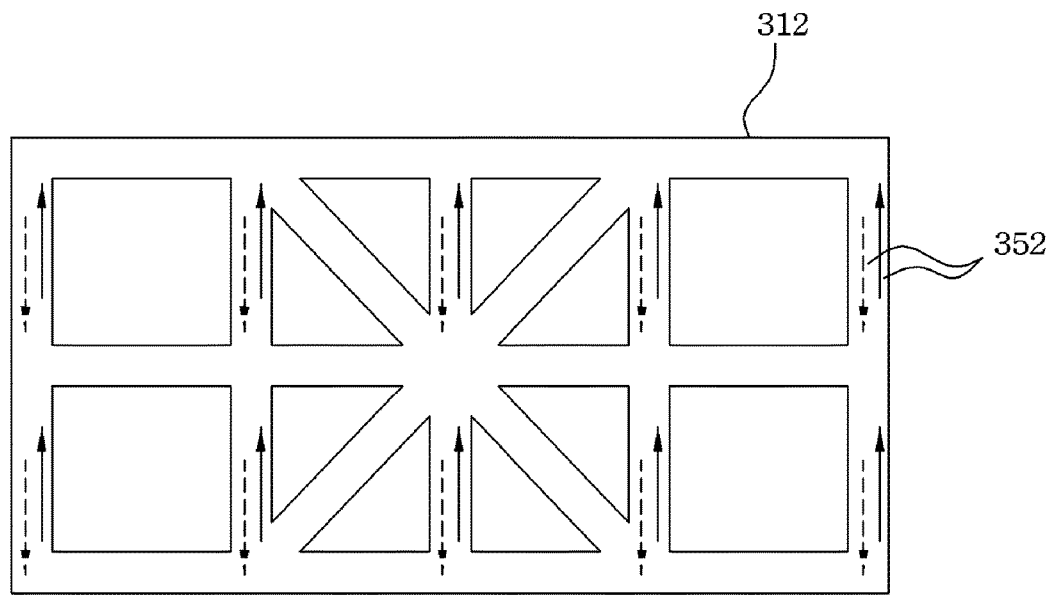
FIGS. 6A to 6D illustrate a device for treating dry eye syndrome and strengthening eyesight according to an exemplary embodiment of the present disclosure.
Figure 6B:
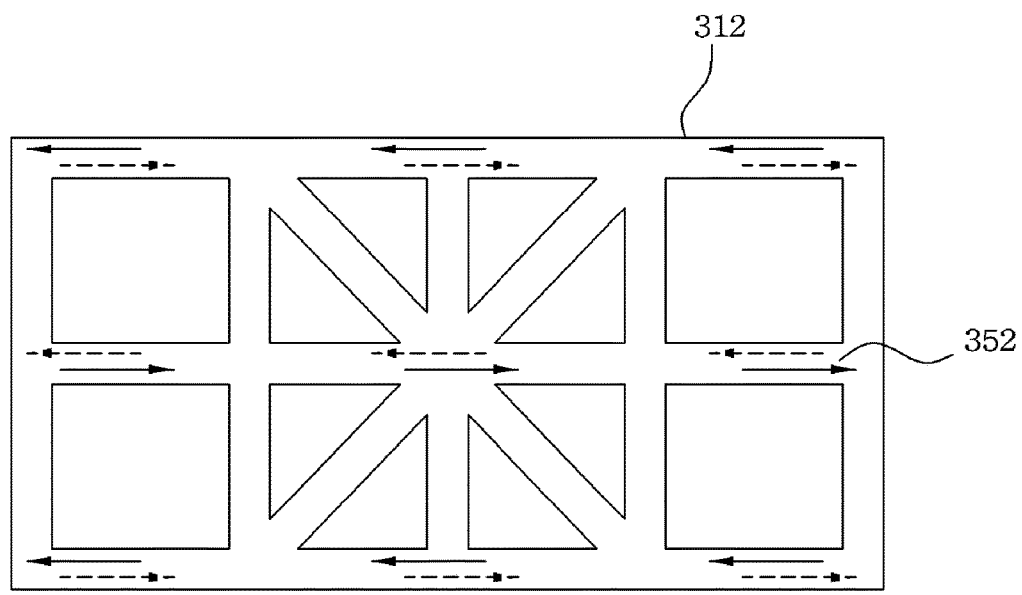
Figure 6C:
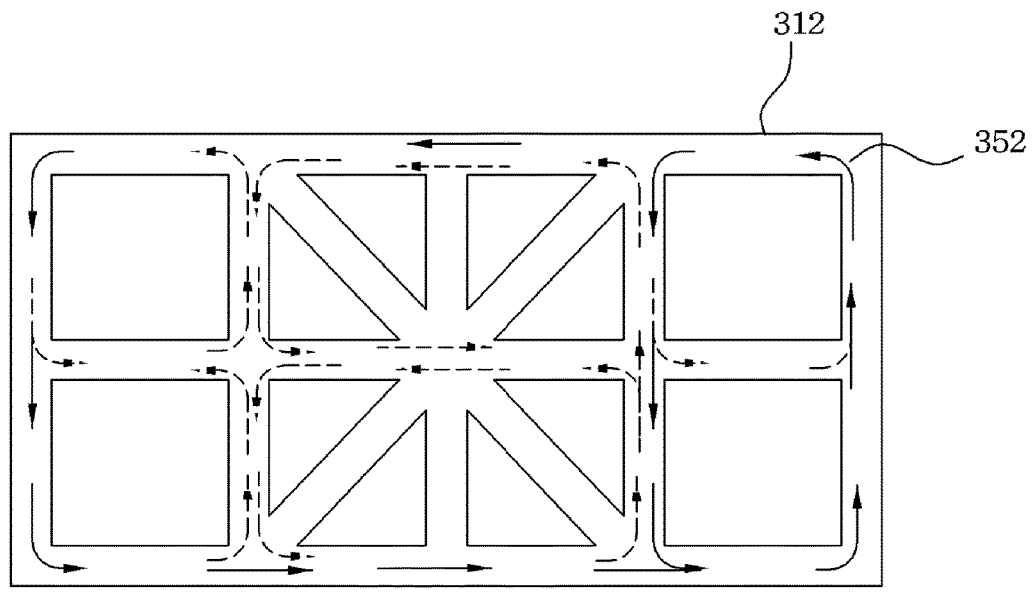
Figure 6D:
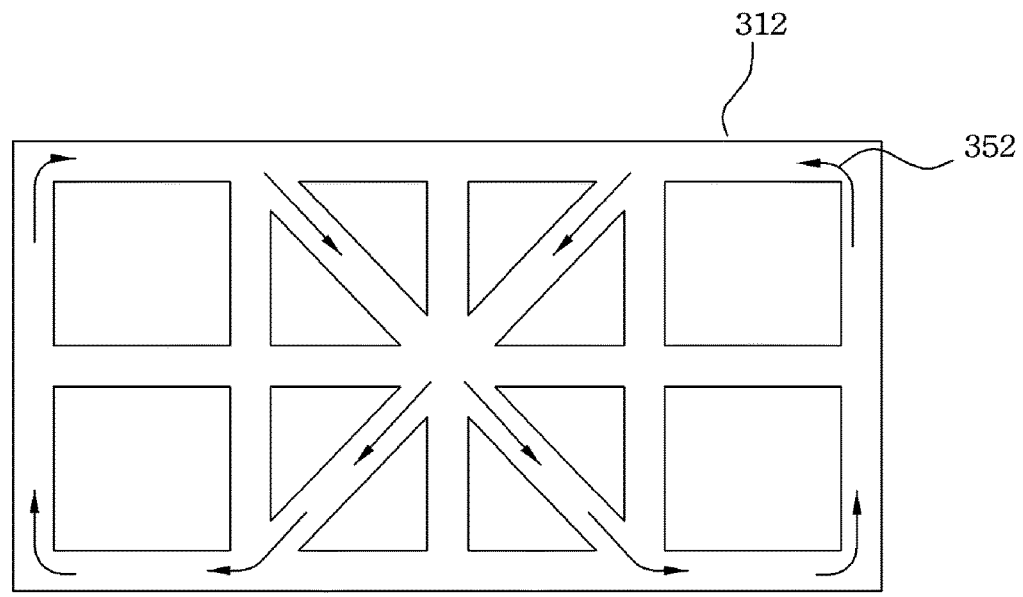
Figure 7:
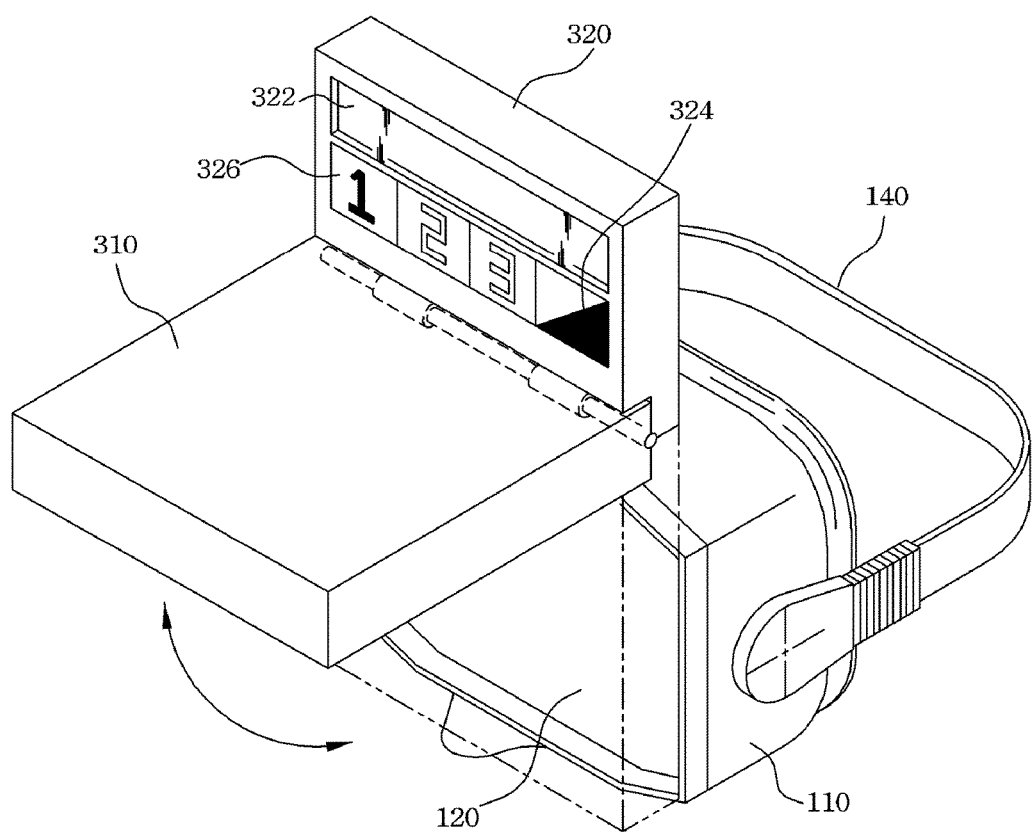
FIG. 7 illustrates a device for treating dry eye syndrome and strengthening eyesight in use, according to an exemplary embodiment of the present disclosure.

FIGS. 1 and 2 are perspective views of a device for treating dry eye syndrome and strengthening eyesight according to an exemplary embodiment of the present disclosure, FIG. 3 is a cross-sectional view illustrating a device for treating dry eye syndrome and strengthening eyesight in an assembled state, according to an exemplary embodiment of the present disclosure, FIG. 4 is a side view of a device for treating dry eye syndrome and strengthening eyesight according to an exemplary embodiment of the present disclosure, FIGS. 5A and 5B illustrate main portions of a device for treating dry eye syndrome and strengthening eyesight according to an exemplary embodiment of the present disclosure, FIGS. 6A to 6D illustrate a device for treating dry eye syndrome and strengthening eyesight according to an exemplary embodiment of the present disclosure, and FIG. 7 illustrates a device for treating dry eye syndrome and strengthening eyesight in use, according to an exemplary embodiment of the present disclosure.

As illustrated, a device for treating dry eye syndrome and strengthening eyesight according to exemplary embodiments of the present disclosure include a water goggles main body part 100, a saline solution container 200 separably coupled to an upper part of the water goggles main body part 100 to store saline solution therein and to feed saline solution into the water goggles main body part 100, and a display device 300 in which a line-of-vision guidance driving part 350 is executed so that the ocular muscle exercise can be performed.

The water goggles main body part 100 has a saline solution container 200 coupled to an upper part thereof, and also includes a mask part 110 through which saline solution is fed inside, a penetrating window 120 formed from transparent material and positioned in front of the mask part 110, an adhesion pad 130 in close adhesion against facial surface of a user, a securing band 140 for securing the device for treating dry eye syndrome and strengthening eyesight onto the facial surface, and a saline solution feeding pipe 150 connected to the saline solution container 200 to feed the saline solution into the mask part 110.

The mask part 110 is where the saline solution is supplied from the saline solution container 200 to the eyeballs of the user positioned therein, thereby increasing humidity of the eyeballs and enabling ocular muscle exercise to be performed in the saline solution.

Such mask part 110 has the penetrating window 120 securely coupled to a front part to provide a user wearing the mask part 110 with an external vision.

The penetrating window 120 is formed of tempered glass resistant to external impact and is configured to perform ocular muscle strengthening exercise inside the mask part 110 filled with saline solution, according to the line-of-vision guidance driving part 350 provided at the display device 300.

Such penetrating window 120 is securely coupled to a front portion of the mask part 110. It is of course possible that more watertight packings 122 may be provided to prevent leakage of the saline solution received in the mask part 110.

Further, an adhesion pad 130 is provided on a circumferential surface of a rear portion of the mask part 110 to allow the mask part 110 to be brought into a closer contact with the facial surface of the user, thus preventing external leakage of the saline solution while being supplied into the mask part 110.

The adhesion pad 130 herein may be configured with a predetermined elasticity that allows the adhesion pad 130 to deform according to the facial surface of the user such that, during adhesion, the adhesion pad 130 is brought into a completely tight contact with the facial surface of the user due to a difference between internal pressure of the mask part 110 and external atmospheric pressure.

Specifically, the adhesion pad 130 according to the present disclosure may preferably be configured to accept the eyeballs and nose of the user so as to enable the user to perform mouth breathing when using the device for treating dry eye syndrome and strengthening eyesight.

Further, the securing band 140 is configured on both sides of the mask part 110 to allow the user to wear the device for treating dry eye syndrome and strengthening eyesight according to the present disclosure. Such securing band 140 is provided with a length adjusting member 142 having a bellows configuration to provide the user wearing the same with most comfortable experience of use, and is also provided with a rotating hinge 144 formed at an end thereof to be rotatably coupled with the mask part 110, thus allowing the securing band 140 to be worn on a head of the user.

In addition, the saline solution container 200 is separably coupled to the upper surface of the mask part 110, and a saline solution feeding pipe 150 is also provided to permit the saline solution to be fed into the mask part 110.

A plurality of (at least two) saline solution feeding pipes 150 may be formed at opposed locations to each other, having a feeding hole 152 whose upper end is in fluid communication with a feed rate adjusting part 230 (to be described below) of the saline solution container 200 and lower end is in fluid communication with an internal space of the mask part 110, such that the saline solution stored in the saline solution container 200 can be fed into the mask part 110 according to an operation of the feed rate adjusting part 230.

The saline solution container 200 includes a storage tank 210 to store saline solution, a sealing lid 220 openably formed on an upper part of the storage tank 210, a saline solution supply housing 240 to feed the stored saline solution to a direction of the mask part 110, and a feed rate adjusting part 230 rotatably coupled to the supply housing 240 to adjust the feed rate of the stored saline solution.

The storage tank 210 is an enclosure formed with an open upper portion, and is separably coupled to an upper end of the mask part 110. A storage groove 202 for storing saline solution therein is formed in the storage tank 210, and rail grooves 214 are formed on both sides of the open upper portion to be slidably engaged with the sealing lid 220.

In this example, guide rails 224 to be slidably inserted into the rail grooves 214 may be formed on both sides of the sealing lid 220, and a handle member 222 may be additionally formed on one surface of the upper part to facilitate sliding operation.

Further, a fixing part 212 for separably coupling with the display device 300 may be configured in front of the storage tank 210 such that, during dry eye syndrome treatment, a user may perform exercise while checking eye strengthening program provided through the display device 300 through the penetrating window 120 of the mask part 110.

In other words, according to the present disclosure, the fixing part 212 may be configured on a front surface of the storage tank 210 so that the line-of-vision guidance driving part 350 of the display device 300 (to be described) is positioned on a same line as the position of the penetrating window 120 of the mask part 110, and may be configured at least two times in front of the storage tank 210 so as to increase a fixing force between the saline solution container 200 and the display device 300.

Although the fixing part 212 is illustrated herein as a triangular shape, the exemplary embodiments are not limited thereto. Accordingly, the fixing part 212 may take on a polygonal shape such as quadrangle, hexagon, and so on, or circle, oval, and so on, as long as the saline solution container 200 and the display device 300 can be separably coupled with each other.

Meanwhile, according to the present disclosure, the saline solution container 200 includes the feed rate adjusting part 230 capable of adjusting a feed rate of the saline solution being fed into the mask part 110, and the supply housing 240 which enables the feed rate adjusting part 230 to adjust the feed rate of the saline solution by a rotational operation.

In an example, the supply housing 240 is formed on both inner sides of the storage tank 210, and the feed rate adjusting part 230 is protruded inside the supply housing 240 inwardly to be rotatably coupled with the feed rate adjusting part 230. Further, a fixing groove 244 is also formed so as to securely receive the saline solution feeding pipe 150 formed on the mask part 110 inserted therein.

The fixing groove 244 is formed to share the same center as an opening and closing hole 238 of the feed rate adjusting part 230 so as to be selectively connected to the opening and closing hole 238 according to whether the feed rate adjusting part 230 is operated or not.

That is, according to the present disclosure, the opening and closing hole 238, the fixing groove 244, and the feeding hole 152 are positioned on the same center line as one another so that the saline solution stored in the storage tank 210 is fed into the mask part 110.

In addition, the upper leading edge of the saline solution feeding pipe 150 is preferably positioned on the same line as the upper leading edge of the fixing groove 244 so as not to be interfered with the saline solution feeding pipe 150 during rotational operation of the feed rate adjusting part 230.

Further, the supply housing 240 includes an inlet hole 246 formed in an upper side, through which an inflow of the saline solution storage from the storage tank 210 is fed into the adjusting housing 232 of the feed rate adjusting part 230.

The feed rate adjusting part 230 is rotatably coupled inside the supply housing 240, and includes an adjusting housing 232 configured to receive a supply of the saline solution from the storage tank 210 through the inlet hole 246 of the supply housing 240, and an adjusting switch 234 exposed to outside the storage tank 210 to be operated by the user to rotate the adjusting housing 232.

In this example, a feeding hole 236 sharing the same center as the inlet hole 246 described above is formed on the upper side of the adjusting housing 232, so that the inflow of saline solution through the inlet hole 246 can be fed into the adjusting housing 232 through the feeding hole 236.

Further, the opening and closing hole 238 is formed on a lower side of the adjusting housing 232, to feed the supply of the saline solution from the storage tank 210 is selectively fed into the mask part 110 through the fixing groove 244 and the inlet hole 152.

According to the feed rate adjusting part 230 described above, when the user rotates the adjusting switch 234 to feed the saline solution into the mask part 110, the adjusting housing 232 connected to the adjusting switch 234 is rotated about the rotation support 242 to thus operate the inlet hole 246 and the feeding hole 236 of the supply housing 240. As a result, the saline solution stored in the storage tank 210 is fed into the adjusting housing 232 of the feed rate adjusting part 230.

In the above example, the opening and closing hole 238 is in a position fluidly communicating with the fixing groove 244 and the feeding hole 152, and the saline solution fed into the adjusting housing 232 is fed into the mask part 110 as it is discharged through the opening and closing hole 238.

Meanwhile, according to the present disclosure, the supply housing 240 may be formed in a shape having an upper part that is open, in which case the saline solution stored in the storage tank 210 may be directly fed into the mask part 110 through the opening and closing hole 238.

The display device 300 is positioned in front of the penetrating window 120, and includes an ocular muscle strengthening part 310 for executing the ocular muscle strengthening program, and an operation controller 320 to control driving of the ocular muscle strengthening part 310.

Further, according to the present disclosure, the display device 300 may additionally include the line-of-vision guidance driving part 350 for implementing ocular muscle strengthening program according to which the user can perform ocular muscle strengthening exercise under control of the operation controller 320, a power supply 360 to supply power necessary to drive the display device 300, and an opening and closing cover 362 to open or close one side of the display device 300 to thus facilitate replacement of the power supply 360.

In the display device 300 described above, the ocular muscle strengthening part 310 is formed below the operation controller 320 and rotatable to a predetermined angle, such that the user has an ability to discern objects outside while wearing the mask part 110.

In other words, according to the present disclosure, an axis support member 332 to receive a rotating axis 330 inserted therein is formed on a lower portion of an operation controller 320 to allow rotatable coupling of the ocular muscle strengthening part 310, and a rotating hole 334 is formed on an upper portion of the ocular muscle strengthening part 310 such that the axis support member 332 described above is inserted in the rotating hole 334 and rotated about the rotating axis 330.

Meanwhile, according to the present disclosure, the ocular muscle strengthening part 310 provided in the display device 300 includes a liquid crystal display (LCD) 352 embedded therein, which makes bar-shaped arrow form to guide a direction of the eyeball exercise according to a predetermined route. In addition, a guidance indicating device 312 having an LCD panel for setting an order and location of emitting light of the LCD 352 is provided.

In an example, the guidance indicating device 312 is configured to output ocular muscle strengthening program to strengthen ocular muscles through the line-of-vision guidance driving part 350 driven by the operation controller 320 to allow a user to strengthen ocular muscles in the mask part 110 and through the indicating window 120.

That is, the guidance indicating device 312 according to the present disclosure provides stepwise ocular muscle strengthening exercise through the line-of-vision guidance driving part 350, and as illustrated in FIG. 5A, ocular muscle strengthening step 1 is executed such that the LCD 352, which is illuminated upon driving of the line-of-vision driving part 350, is illuminated repeatedly in up and down directions, along a path on the LCD panel formed on the guidance indicating device 312.

Further, as illustrated in FIG. 5B, when the time set by the operation controller 320 (to be described) for the ocular muscle strengthening step 1 elapses, ocular muscle strengthening step 2 is then executed, in which illumination is provided repeatedly in left and right directions along the path on the LCD panel, thus guiding the line of vision of the user to obtain ocular muscle strengthening effect.

Further, as illustrated in FIG. 5C, after the ocular muscle strengthening step 2 described above, ocular muscle strengthening step 3 is then executed, in which the LCD 352 is illuminated in a bar-like form, while circulating in a circle along a path on the LCD panel in a clockwise direction, so that the line of vision of the user is guided in a way of strengthening ocular muscle.

Then, as illustrated in FIG. 5D, ocular muscle strengthening step 4 is executed, in which the LCD 352 is illuminated in a bar-like form, and illuminated along a path on the LCD panel in a pattern having a "Figure-8" (or double-loop) shape. Therefore, a variety of ocular muscle strengthening steps are provided.

As described above, the display device 300 may provide sequential steps of ocular muscle strengthening exercise, but not limited thereto. Accordingly, it is possible that only certain step(s) as desired by the user may be repeatedly executed, or the ocular muscle strengthening exercise may be performed in a reverse order to that described above.

Further, the operation controller 320 provided in the display device 300 is separably coupled to the storage tank 210 of the saline solution container 200 described above so that the ocular muscle strengthening part 310 is positioned in the mask part 110, to control the driving of the ocular muscle strengthening part 310 and simultaneously set the duration of driving the line-of-vision guidance driving part 350, driving steps thereof, and so on.

Such operation controller 320 includes a fixing means 340 on a rear face, which is inserted into a fixing part 212 formed on the storage tank 210 to fix the display device 300 to the saline solution container 200.

The fixing means 340 includes a fixing flange 342 extending on a rear portion of the operation controller 320 to provide a predetermined supporting force upon coupling with the saline solution container 200, and a fixing protrusion 334 extending downward from the fixing flange 342 in an identical shape as the fixing part 212 to be inserted.

According to the present disclosure, the operation controller 320 described above includes a setting indicating part 322 for outputting setting of the line-of-vision guidance driving part 350, a driving setting part 324 for setting the condition of driving the line-of-vision guidance driving part 350 provided in the ocular muscle strengthening part 310, i.e., for setting the ocular muscle strengthening steps, and a timer setting part 326 for setting duration of driving the line-of-vision guidance driving part 350.

The setting indicating part 322 is an element for indicating pre-setting data before the line-of-vision guidance driving part 350 is driven.

The setting indicating part 322 indicates the data as set through the driving setting part 324 and the timer setting part 326 to enable a user outside to notice the current status of the line-of-vision guidance driving part 350.

That is, the setting indicating part 322 displays the ocular muscle strengthening program steps being performed by the line-of-vision driving part 350 to enable a user to confirm which step of the ocular muscle strengthening exercise that he or she is currently performing, and also outputs the set duration of time and remaining time of the ocular muscle strengthening exercise for the user's notice.

The driving setting part 324 is configured to set and control as to whether the line-of-vision guidance driving part 350 is to be driven or not, and control the power supply to stop the line-of-vision guidance driving part 350 when the exercise time as set through the timer setting part 326 elapses.

The driving setting part 324 described above is configured to supply the power toward the line-of-vision guidance driving part 350 through a power supply part 360 provided in the ocular muscle strengthening part 310, or to block the power supply.

Further, the driving setting part 324 is preferably provided with a power supply on/off button to allow the user to drive or stop. For example, a long press on the power supply on/off button may force the line-of-vision guidance driving part 350 to stop. The driving setting part 324 may also be configured to output an alarm through a speaker or the like for 0.2 seconds, thus notifying the exercise will begin, as a preparatory operation before the line-of-vision guidance driving part 350 is driven.

The timer setting part 326 is configured to set the duration of time of driving the line-of-vision guidance driving part 350 is driven so as to control the duration of time the LCD 350 is illuminated on the LCD panel of the guidance indicating part 312. In an exemplary embodiment, the duration of time is illustrated as being set based on a unit of 1 minute, such as, 1 minute, 2 minutes, 3 minutes, and so on, but not limited thereto.

Accordingly, the range of setting the time at the timer setting part 326 by the driving setting part 324 may be on the basis of unit of seconds, 5 minutes, 10 minutes, and so on.

As described above, when the operation controller 320 sets the duration of driving the line-of-vision guidance driving part 350 of the ocular muscle strengthening part 310 by the timer setting part 326, the LCD 352 is illuminated on the LCD panel of the guidance indicating device 312 in an arrow-like form, and continuously repeated in directions in an order of up, down, left, right, clockwise and rotating in the Figure-8 pattern. As a result, a variety of ocular muscle strengthening exercise is performed.

With a device for treating dry eye syndrome and strengthening eyesight configured as described above according to the present disclosure, the hygienic management of the therapeutic device is easy since the saline solution container 200 and the water goggles main body part 100 are configured so as to be separable, and there is an effect of treating dry eye syndrome and improving eyesight while allowing the user to breath freely in a comfortable state by allowing the muscular exercise of the eyes to be carried out in the saline solution in the state in which the facial surface of the user is closely adhered to the water goggles main body part. As a result, the user is able to perform ocular muscle exercise, and also cleanse eyes to remove wastes from the eyes, which promotes blood circulation around eyes and delaying or preventing weakening of eyesight.

That is, the foregoing exemplary embodiments are merely exemplary and are not to be construed as limiting the exemplary embodiments, and the scope of the present disclosure is represented by the accompanying claims, and meaning and breadth of the claims, and all the modifications or modified forms derived from the equivalent concept thereof should be interpreted as being included in the scope of the present disclosure.

INDUSTRIAL APPLICABILITY

The present disclosure relates to a device for treating dry eye syndrome and strengthening eyesight, and is applicable to the field of industry for medical equipment for vision care and ocular exercise equipment industry.

The invention claimed is:

1. A device for treating dry eye syndrome and strengthening eyesight, comprising:
   a water goggles main body part into which a saline solution is injected and which is closely adhered to a facial surface of a user, thereby allowing muscular exercise of eyeballs to be carried out in the saline solution;
   a saline solution container coupled to an upper part of the water goggles main body part so as to supply a predetermined amount of saline solution; and
   a display device fixed to a front of the saline solution container, and in which an ocular muscle strengthening program for guiding the user's line of vision is executed so as to enable eyeball exercise to be performed in the saline solution.

2. The device of claim 1, wherein the water goggles main body part comprising:
   a mask part to which the saline solution is supplied from the saline solution container in a state in which the facial surface of the user is in position;
   a penetrating window formed of a transparent material, fixed to a front of the mask part;
   an adhesion pad for bringing the facial surface of a user to a close contact with the mask part;
   a securing band configured to allow the user to wear the water goggles main part on the user's head; and
   a saline solution feeding pipe protruding upward from an upper part of the mask part to be coupled with the saline solution container, to inject the saline solution into the mask part.

3. The device of claim 1 further comprising:
   a storage tank for storing the saline solution;
   a fixing part formed on the front of the storage tank to securely receive the display device inserted therein;
   a sealing lid openably formed on an upper part of the storage tank;
   a supply housing for supplying the stored saline solution into the water goggles main body part; and
   a feed rate adjusting part rotatably coupled with the supply housing to adjust a feed rate of the saline solution being supplied toward the water goggles main body part.

4. The device of claim 3, wherein the supply housing comprising:
   a rotation support inwardly protruded to be rotatably coupled with the feed rate adjusting part;
   an inlet hole through which the saline solution stored in the storage tank is introduced into the feed rate adjusting part; and
   a fixing groove coupled with the water goggles main body part to supply the saline solution stored in the storage tank toward the water goggles main body part.

5. The device of claim 4, wherein the feed rate adjusting part comprising:
   an adjusting housing coupled at one end with the rotation support, and supplying the saline solution through a supply hole fluidly communicating with the inlet hole, the adjusting housing including an opening and closing hole for discharging the supplied saline solution toward the water goggles main body part; and
   an adjusting switch formed at other end of the adjusting housing, to adjust a feed rate of the saline solution by controlling opening and closing of the opening and closing hole.

6. The device of claim 1, wherein the display device comprising:
   an ocular muscle strengthening part positioned in front of the water goggles main body part to perform an ocular muscle strengthening program;
   a line-of-vision guidance driving part for executing the ocular muscle strengthening program in association with the ocular muscle strengthening part to thus enable the user to perform an ocular muscle strengthening exercise; and
   an operation controller fixed to the saline solution container to control driving of the ocular muscle strengthening part and set duration of driving the line-of-vision guidance driving part and driving step thereof.

7. The device of claim 6, wherein the ocular muscle strengthening part and the operation controller are rotatably coupled by a rotating axis.

8. The device of claim 6 further comprising a guidance indicating device in the ocular muscle strengthening part, wherein the guidance indicating device comprises a liquid crystal display (LCD) illuminated upon driving of the line-of-vision guidance driving part, and a LCD panel having the LCD installed therein.

9. The device of claim 8, wherein, upon driving of the line-of-vision guidance driving part, the guidance indicating device causes the LCD to be illuminated in an arrow-like form and repeated in directions in an order of up, down, left, right, clockwise, and rotating in a Figure-8 pattern.

10. The device of claim 6, wherein the operation controller further comprises a fixing means formed on a rear face to fix the display device to the saline solution container.

11. The device of claim 6, wherein the operation controller comprising:
    a setting indicating part for outputting setting status of the line-of-vision guidance driving part;
    a driving setting part for setting an ocular muscle strengthening step of the ocular muscle strengthening program executed by the line-of-vision guidance driving part; and
    a timer setting part for setting a duration of driving the line-of-vision driving part.

12. The device of claim 11, wherein the driving setting part comprises a power supply on/off button with which a user selects between driving and stopping, and when the line-of-vision guidance driving part is driven, the driving setting part outputs an alarm for 0.2 second as a preparatory operation, notifying that the exercise will begin.

13. A device for treating dry eye syndrome and strengthening eyesight, comprising:
    a water goggles main body part into which a saline solution is injected and which is closely adhered to a facial surface of a user;
    a saline solution container coupled to an upper part of the water goggles main body part; and
    a display device fixed to a front of the saline solution container, and in which an ocular muscle strengthening program for guiding the user's line of vision is executed,
    wherein the display device comprising:
       an ocular muscle strengthening part positioned in front of the water goggles main body part;
       a line-of-vision guidance driving part for executing the ocular muscle strengthening program in association with the ocular muscle strengthening part; and
       an operation controller fixed to the saline solution container.

14. The device of claim 13, wherein the ocular muscle strengthening part and the operation controller are rotatably coupled by a rotating axis.

15. The device of claim 13 further comprising a guidance indicating device in the ocular muscle strengthening part, wherein the guidance indicating device comprises a liquid crystal display (LCD) illuminated upon driving of the line-of-vision guidance driving part, and a LCD panel having the LCD installed therein.

16. The device of claim 15, wherein, upon driving of the line-of-vision guidance driving part, the guidance indicating device causes the LCD to be illuminated in an arrow-like form and repeated in directions in an order of up, down, left, right, clockwise, and rotating in a FIG.-8 pattern.

17. The device of claim 13, wherein the operation controller further comprises a fixing means formed on a rear face to fix the display device to the saline solution container.

18. The device of claim 13, wherein the operation controller comprising:
   a setting indicating part for outputting setting status of the line-of-vision guidance driving part;
   a driving setting part for setting an ocular muscle strengthening step of the ocular muscle strengthening program executed by the line-of-vision guidance driving part; and
   a timer setting part for setting a duration of driving the line-of-vision driving part.

19. The device of claim 18, wherein the driving setting part comprises a power supply on/off button with which a user selects between driving and stopping, and when the line-of-vision guidance driving part is driven, the driving setting part outputs an alarm for 0.2 second as a preparatory operation, notifying that the exercise will begin.

* * * * *